(12) United States Patent
Ostrander et al.

(10) Patent No.: US 9,179,260 B2
(45) Date of Patent: Nov. 3, 2015

(54) MEDICAMENT INFORMATION SYSTEM AND METHOD

(71) Applicant: Mylan, Inc., Morgantown, WV (US)

(72) Inventors: Kevin Ostrander, Ringoes, NJ (US); John Denny, Morgantown, WV (US)

(73) Assignee: Mylan Inc., Morgantown, WV (US)

( * ) Notice: Subject to any disclaimer, the term of this patent is extended or adjusted under 35 U.S.C. 154(b) by 0 days.

(21) Appl. No.: 14/460,169

(22) Filed: Aug. 14, 2014

(65) Prior Publication Data

US 2014/0357304 A1    Dec. 4, 2014

Related U.S. Application Data

(63) Continuation-in-part of application No. 13/907,028, filed on May 31, 2013.

(60) Provisional application No. 61/732,753, filed on Dec. 3, 2012.

(51) Int. Cl.
*G08B 23/00* (2006.01)
*H04W 4/02* (2009.01)
(Continued)

(52) U.S. Cl.
CPC ............... *H04W 4/023* (2013.01); *A61M 5/20* (2013.01); *A61M 5/5086* (2013.01); *B65D 83/02* (2013.01); *G06F 19/3456* (2013.01)

(58) Field of Classification Search
CPC ............ G06F 19/3418; G06F 19/3412; G06F 19/3406; G06F 17/30032; A61B 5/1112; A61B 5/0002; A61B 5/0022; A61B 5/1113; A61B 5/002; G08B 21/0211; G08B 21/245; G08B 25/008; G08B 25/009

USPC .................. 340/539.11–539.14; 128/200.14, 128/200.21, 200.23, 203.12, 204.23
See application file for complete search history.

(56) References Cited

U.S. PATENT DOCUMENTS 4,031,893 A    6/1977    Kaplan et al.
4,394,863 A    7/1983    Bartner
(Continued)

FOREIGN PATENT DOCUMENTS

EP    1 291 802    3/2003
WO    WO 96/21925    7/1996
(Continued)

OTHER PUBLICATIONS

International Search Report for PCT/US2013/072881 dated Feb. 26, 2014.
(Continued)

*Primary Examiner* — Brian Zimmerman
*Assistant Examiner* — Thomas McCormack
(74) *Attorney, Agent, or Firm* — Knobbe Martens Olson & Bear LLP

(57) ABSTRACT

Various exemplary embodiments relate to a method, device, and storage medium including one or more of the following: receiving location information and expiration information; determining a current location of the mobile device; determining that the medicament device is within a predetermined distance from the mobile device; determining that the medicament device is currently associated with an expiration event; outputting an expiration alarm indicating the expiration event in response to determining that the medicament device is within a predetermined distance from the mobile device and that the medicament device is currently associated with an expiration event; receiving, from the user, a request to display a map of a geographic area; displaying, by the mobile device and via a non-operating system application, the map of the geographic area; and displaying an alert icon on the map, wherein the location of the icon on the map is based on the received location information.

20 Claims, 10 Drawing Sheets

(51) Int. Cl.
  *G06F 19/00* (2011.01)
  *A61M 5/20* (2006.01)
  *A61M 5/50* (2006.01)
  *B65D 83/02* (2006.01)

(56) References Cited

U.S. PATENT DOCUMENTS

| | | | |
|---|---|---|---|
| 4,484,910 A | 11/1984 | Sarnoff et al. |
| 4,640,686 A | 2/1987 | Dalling et al. |
| 4,663,621 A | 5/1987 | Field et al. |
| 4,678,461 A | 7/1987 | Mesa |
| 4,731,765 A | 3/1988 | Cole et al. |
| 4,795,433 A | 1/1989 | Sarnoff |
| 4,832,682 A | 5/1989 | Sarnoff |
| 5,085,641 A | 2/1992 | Sarnoff et al. |
| 5,092,843 A | 3/1992 | Monroe et al. |
| 5,102,393 A | 4/1992 | Sarnoff et al. |
| 5,221,024 A | 6/1993 | Campbell |
| 5,354,286 A | 10/1994 | Mesa et al. |
| 5,710,551 A | 1/1998 | Ridgeway |
| 5,815,586 A | 9/1998 | Dobbins |
| 5,835,455 A | 11/1998 | Hanson et al. |
| 5,967,975 A | 10/1999 | Ridgeway |
| 6,109,774 A | 8/2000 | Holmes et al. |
| 6,158,613 A | 12/2000 | Novosel et al. |
| 6,401,991 B1 | 6/2002 | Eannone |
| 6,471,087 B1 | 10/2002 | Shusterman |
| 6,633,796 B1 | 10/2003 | Pool et al. |
| 6,707,763 B2 | 3/2004 | Osberg et al. |
| 6,825,753 B2 | 11/2004 | Cardinale et al. |
| 6,880,722 B2 | 4/2005 | Anderson et al. |
| 6,937,150 B2 | 8/2005 | Medema et al. |
| 6,941,274 B1 | 9/2005 | Ramachandran et al. |
| 7,449,012 B2 | 11/2008 | Young et al. |
| 7,715,277 B2 | 5/2010 | de la Huerga |
| 7,749,194 B2 | 7/2010 | Edwards et al. |
| 7,941,534 B2 | 5/2011 | De La Huerga |
| 8,048,035 B2 | 11/2011 | Mesa et al. |
| 8,487,738 B2 | 7/2013 | Faries, Jr. et al. |
| 8,544,645 B2 | 10/2013 | Edwards et al. |
| 8,593,278 B2 | 11/2013 | Churbock et al. |
| 8,744,620 B2 | 6/2014 | Shavelsky et al. |
| 8,753,308 B2 | 6/2014 | Palmer et al. |
| 2002/0100472 A1 | 8/2002 | Casper et al. |
| 2003/0023146 A1 | 1/2003 | Shusterman, D.O. |
| 2003/0090364 A1 | 5/2003 | Cardinale et al. |
| 2004/0099676 A1 | 5/2004 | Anderson et al. |
| 2004/0158350 A1 | 8/2004 | Ostergaard et al. |
| 2005/0005934 A1 | 1/2005 | Harvey |
| 2005/0146419 A1 | 7/2005 | Porter |
| 2006/0089545 A1 | 4/2006 | Ratjen et al. |
| 2007/0186923 A1 | 8/2007 | Poutiatine et al. |
| 2007/0197968 A1 | 8/2007 | Pongpairochana et al. |
| 2007/0204497 A1 | 9/2007 | de la Huerga |
| 2007/0233001 A1 | 10/2007 | Burroughs et al. |
| 2008/0188813 A1 | 8/2008 | Miller et al. |
| 2008/0249468 A1 | 10/2008 | Edwards et al. |
| 2009/0030366 A1 | 1/2009 | Hochman |
| 2009/0120962 A1 | 5/2009 | Malorni et al. |
| 2009/0128330 A1 | 5/2009 | Monroe |
| 2009/0184022 A1 | 7/2009 | Coe et al. |
| 2009/0187274 A1 | 7/2009 | Higham |
| 2009/0194104 A1 | 8/2009 | Van Sickle et al. |
| 2010/0022953 A1 | 1/2010 | Bochenko et al. |
| 2010/0022987 A1 | 1/2010 | Bochenko et al. |
| 2010/0062748 A1 | 3/2010 | Steinmetz |
| 2010/0160857 A1 | 6/2010 | Pongpairochana et al. |
| 2010/0204659 A1 | 8/2010 | Bochenko et al. |
| 2010/0305750 A1 | 12/2010 | Conley |
| 2010/0318035 A1 | 12/2010 | Edwards et al. |
| 2011/0166700 A1 | 7/2011 | Dunn |
| 2011/0234419 A1 | 9/2011 | Churbock et al. |
| 2012/0259456 A1 | 10/2012 | Saltsov |
| 2012/0259458 A1 | 10/2012 | Barrett et al. |
| 2012/0274196 A1 | 11/2012 | Arceta et al. |
| 2013/0030566 A1 | 1/2013 | Shavelsky et al. |
| 2013/0090594 A1 | 4/2013 | Palmer et al. |
| 2013/0131586 A1 | 5/2013 | Poutiatine et al. |
| 2013/0166066 A1 | 6/2013 | Dunn |
| 2014/0114277 A1 | 4/2014 | Eggert et al. |

FOREIGN PATENT DOCUMENTS

| | | |
|---|---|---|
| WO | WO 03/043684 | 5/2003 |
| WO | WO 2005 004961 | 1/2005 |
| WO | WO 2007/081947 | 7/2007 |

OTHER PUBLICATIONS

International Search Report for PCT/US2013/072878 dated Feb. 26, 2014.

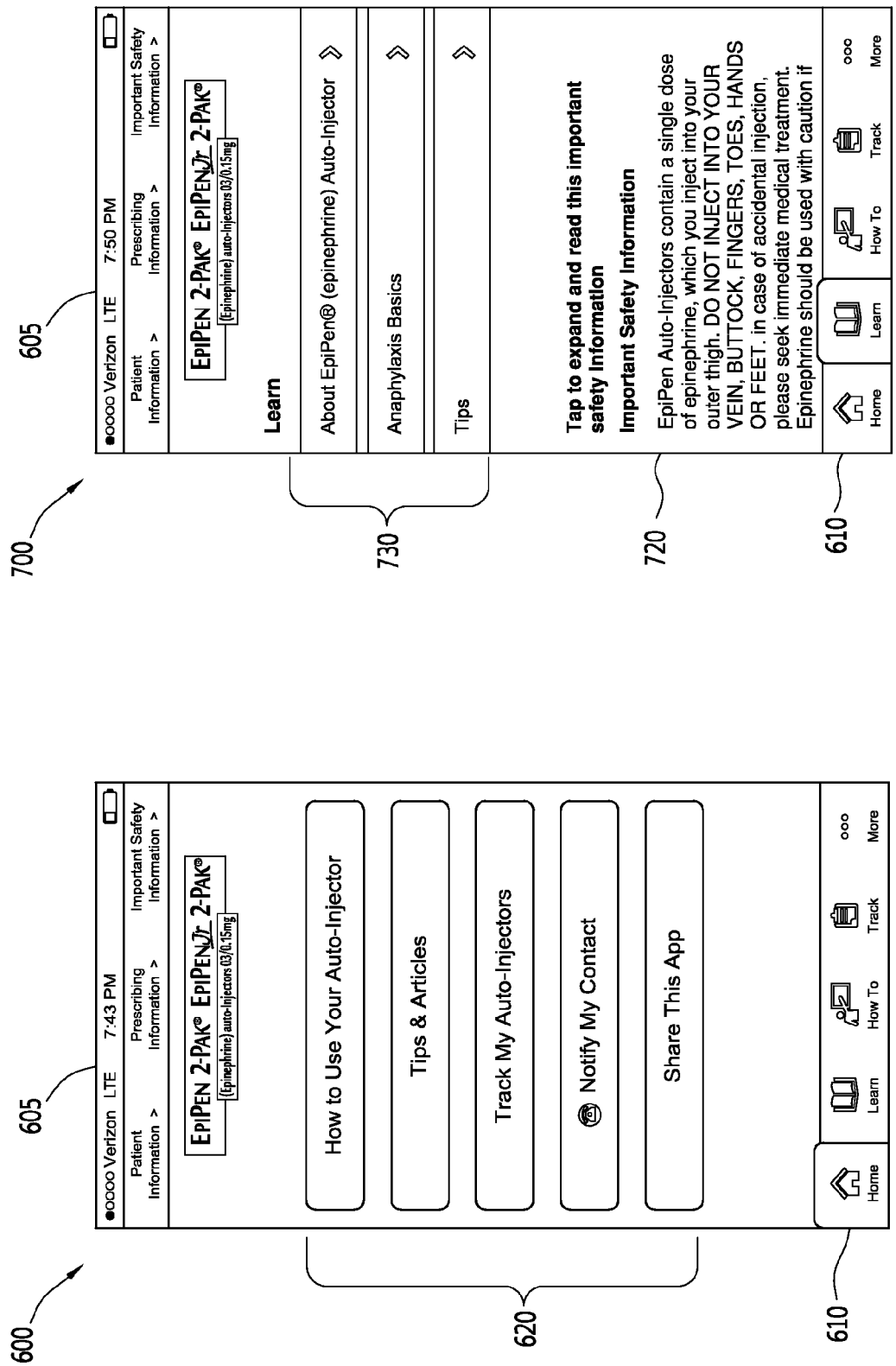

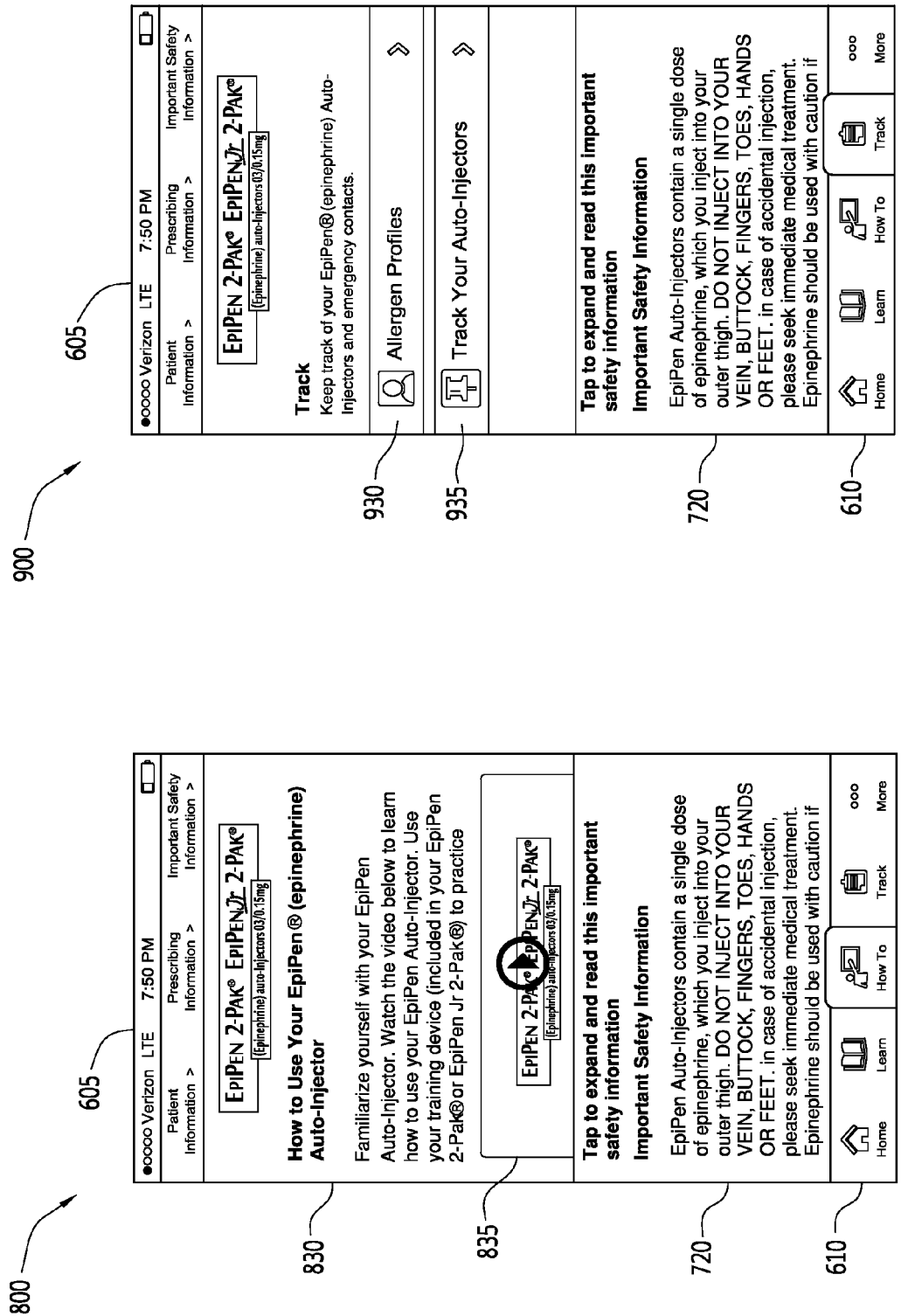

MEDICAMENT INFORMATION SYSTEM AND METHOD

CROSS-REFERENCE TO RELATED APPLICATIONS

This application is a continuation-in-part of U.S. patent application Ser. No. 13/907,028, filed on May 31, 2013, which claims the benefit of U.S. provisional patent application No. 61/732,753, filed on Dec. 3, 2012, the entire disclosures of which are incorporated herein by reference for all purposes.

TECHNICAL FIELD

Various exemplary embodiments disclosed herein relate generally to administration of medicaments.

BACKGROUND

Some people suffer from medical conditions such as severe allergies that may result in anaphylaxis. Anaphylaxis may be treated by administration of epinephrine. Patients may be prescribed an auto-injector of epinephrine to treat sudden anaphylaxis.

Anaphylaxis, however, often leads to an emergency situation wherein epinephrine or other medication should be administered as soon as possible to prevent loss of life or other complications. Proper use of the auto-injector to treat anaphylaxis is therefore important. Patients with medical conditions that may result in anaphylaxis are often inexperienced at providing medical treatment. Use of an auto-injector may also be intimidating for some patients. Moreover, an emergency situation requiring treatment may arise at unexpected times or after a significant time from receiving the auto-injector and instructions for use from a doctor or pharmacist. Additionally, due to the unpredictable times at which need for the auto-injector arise, the medicament may expire before the auto-injector is used and, therefore, may not effectively treat anaphylaxis in an emergency situation.

SUMMARY

In light of the present need for various contingency planning in the administration of epinephrine and other medications, a brief summary of various exemplary embodiments is presented. Some simplifications and omissions may be made in the following summary, which is intended to highlight and introduce some aspects of the various exemplary embodiments, but not to limit the scope of the invention. Detailed descriptions of a preferred exemplary embodiment adequate to allow those of ordinary skill in the art to make and use the inventive concepts will follow in later sections.

Various exemplary embodiments relate to a method of using an emergency medicament device. The method includes reading an ID tag from the medicament device using a mobile device; automatically requesting instructions for using the medicament device based on the ID tag; and displaying a video to a user of the mobile device, the video providing instructions for using the medicament device in accordance with approved labeling of the medicament device.

In various embodiments, the ID tag is a quick response (QR) code.

In various embodiments, the method further includes reading product information including an expiration date from the medicament device; transmitting the product information to an application server; and receiving a notification from the application server regarding the expiration date of the medicament device. The step of reading an expiration date may include photographing a printed expiration date on the medicament device; and recognizing characters in the printed expiration date. The product information may further include a lot number and the method may further include receiving a notification regarding a recall of the medicament device based on the lot number.

In various embodiments, the video is streamed from a remote application server.

In various embodiments, the method further includes receiving an indication that the medicament device has been used; and providing location information to emergency services.

In various embodiments, the method further includes sending registration information to an application server, the registration information including a request to track location information; receiving medicament device information for a registered medicament device including location information; and displaying a map including registered medicament device information.

Various exemplary embodiments relate to an electronic medicament device including: a reservoir configured to store an amount of medication for treating anaphylaxis; an administration component for administering the medication to a patient; a processor communicatively connected to a memory storing medicament device information; and an identification tag configured to be read by another device, the identification tag providing the medicament device information including identification of instructions for using the medicament device.

In various embodiments, the electronic medicament device includes a display device, wherein the processor is configured to display an alert via the display device when an expiration date associated with the amount of medication has been passed.

In various embodiments, the processor is configured to play audio instructions for administering the medication.

In various embodiments, processor is configured to control the amount of medication administered by the administration component.

In various embodiments, administration component is an auto-injector.

In various embodiments, the electronic medicament device further includes a communication interface, wherein the processor is configured to communicate with at least one remote system via the communication interface in response to the occurrence of an event, the event including at least one of: administration of the medication and expiration of the medication.

In various embodiments, the electronic medicament device further includes a temperature sensor configured to determine the current temperature of the medication, wherein the processor is configured to provide an indication that the current temperature is outside of an approved temperature range.

In various embodiments, the electronic medicament device further includes a short-range wireless communication interface, wherein the processor is configured to periodically attempt to connect to an external device via the short-range wireless communication interface and trigger an alarm responsive to the attempt to connect failing.

Various exemplary embodiments relate to an application server in communication with a mobile device, the application server including a processor and a memory, the application server configured to: receive a medicament device identifier scanned from an emergency medicament device containing epinephrine for the treatment of anaphylaxis using an application on the mobile device; and stream an instructional video to the mobile device, the instructional video providing instructions for using the medicament device in accordance with approved labeling of the medicament device.

In various embodiments, the application server is further configured to: receive registration information from the mobile device including an expiration date and lot number scanned from a medicament device and contact information; store the registration information in association with the contact information; determine an event associated with the registration information; and send a notification to the mobile device based on the event and the contact information.

In various embodiments, the event is one of an expiration of the medicament device and a recall of the medicament device.

In various embodiments, the application server is further configured to: periodically receive location information of the medicament device from the mobile device; update a database with the location information for the medicament device; receive a request for location information from a second device; determine whether the second device is allowed to access the location information for the medicament device based on the registration information; and provide medicament device information including the location information to the second device responsive to the second device being allowed to access the location information.

Various embodiments described herein relate to a method of tracking a status of a medicament device by a mobile device, the method including: receiving, by the mobile device, information regarding a medicament device, the information including location information and expiration information; determining a current location of the mobile device; determining, based on comparing the current location to the location information, that the medicament device is within a predetermined distance from the mobile device; determining, based on the received expiration information, that the medicament device is currently associated with an expiration event; outputting, to the user of the mobile device and via an operating system element of the mobile device configured to output notifications from multiple different applications, an expiration alarm indicating the expiration event in response to determining that the medicament device is within a predetermined distance from the mobile device and that the medicament device is currently associated with an expiration event; receiving, from the user, a request to display a map of a geographic area; displaying, by the mobile device and via a non-operating system application, the map of the geographic area; and displaying an alert icon on the map, wherein the location of the icon on the map is based on the received location information.

Various embodiments described herein relate to a mobile device for tracking a status of a medicament device by a mobile device, the method including: a communications interface; a memory; and a processor in communication with the communications interface and the memory, wherein the processor is configured to: receive information regarding a medicament device, the information including location information and expiration information, determine a current location of the mobile device, determine, based on comparing the current location to the location information, that the medicament device is within a predetermined distance from the mobile device; determine, based on the received expiration information, that the medicament device is currently associated with an expiration event, output, to the user of the mobile device and via an operating system element configured to output notifications from multiple different applications, an expiration alarm indicating the expiration event in response to determining that the medicament device is within a predetermined distance from the mobile device and that the medicament device is currently associated with an expiration event, receive, from the user, a request to display a map of a geographic area, display, via a non-operating system application, the map of the geographic area, and display an alert icon on the map, wherein the location of the icon on the map is based on the received location information.

Various embodiments described herein relate to a non-transitory machine-readable storage medium encoded with instructions for execution by a mobile device for tracking a status of a medicament device, the medium including: instructions for receiving, by the mobile device, information regarding a medicament device, the information including location information and expiration information; instructions for determining a current location of the mobile device; instructions for determining, based on comparing the current location to the location information, that the medicament device is within a predetermined distance from the mobile device; instructions for determining, based on the received expiration information, that the medicament device is currently associated with an expiration event; instructions for outputting, to the user of the mobile device and via an operating system element of the mobile device configured to output notifications from multiple different applications, an expiration alarm indicating the expiration event in response to determining that the medicament device is within a predetermined distance from the mobile device and that the medicament device is currently associated with an expiration event; instructions for receiving, from the user, a request to display a map of a geographic area; instructions for displaying, by the mobile device and via a non-operating system application, the map of the geographic area; and instructions for displaying an alert icon on the map, wherein the location of the icon on the map is based on the received location information.

Various embodiments are described wherein the mobile device receives the information regarding the medicament device by optically reading the information from at least one of the medicament device and a packaging of the medicament device.

Various embodiments are described wherein the mobile device receives the information regarding the medicament device by wirelessly communicating with at least one of the medicament device and a packaging of the medicament device.

Various embodiments are described wherein the expiration information is an expiration date and the expiration event includes at least one of a past expiration of the medicament device and an expiration of the medicament device at a future date that is less than a predetermined amount of time from a current date.

Various embodiments are described wherein the mobile device receives the location information from the medicament device via a communications network, whereby the mobile device is capable of receiving the location information from the medicament device when the medicament device is at a location that is remote from the mobile device.

Various embodiments additionally include receiving, by the mobile device via a communications network, an activation indication that a second medicament device has been activated; outputting an activation alert to the user based on the activation indication.

Various embodiments additionally include periodically polling a second medicament device using wireless communication to estimate a distance between the second medicament device and the mobile device; determining, based on the estimated distance, that the second medicament device is farther away from the mobile device than a predetermined allowable distance; and outputting a missing device alarm in response to determining that the second medicament device is farther away from then mobile device than the predetermined allowable distance.

BRIEF DESCRIPTION OF THE DRAWINGS

In order to better understand various exemplary embodiments, reference is made to the accompanying drawings, wherein:

FIG. 6 illustrates a first exemplary user interface for a medicament device tracking application;

FIG. 7 illustrates a second exemplary user interface for a medicament device tracking application;

FIG. 8 illustrates a third exemplary user interface for a medicament device tracking application;

FIG. 9 illustrates a fourth exemplary user interface for a medicament device tracking application;

FIG. 10 illustrates a fifth exemplary user interface for a medicament device tracking application;

FIG. 11 illustrates a sixth exemplary user interface for a medicament device tracking application;

DETAILED DESCRIPTION

Figure 1:
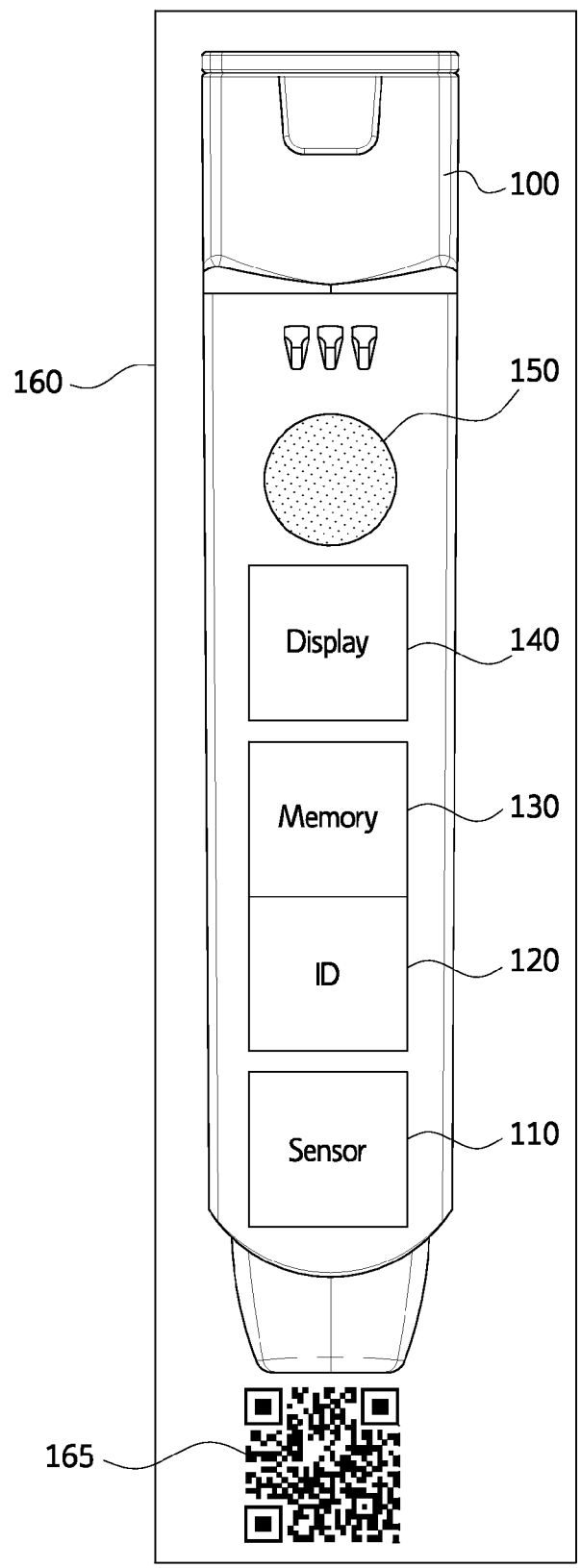
FIG. 1 illustrates an exemplary electronic medicament device.

Referring now to the drawings, in which like numerals refer to like components or steps, there are disclosed broad aspects of various exemplary embodiments.

FIG. 1 illustrates an exemplary electronic medicament device 100. The electronic medicament device 100 may include a medication for treating a condition, the medication being stored in a reservoir. In various exemplary embodiments, the electronic medicament device 100 includes an auto-injector for epinephrine or other administration component such as a non-auto-injector needle or controlled access panel for providing access to a solid medication stored in the reservoir. Medicaments may include one or more medicaments for treating emergency or other medical conditions. In various exemplary embodiments, medicament device 100 may be auto-injectors for administering a dose of epinephrine. Suitable auto-injectors and associated devices and method are described by U.S. Pat. Nos. 4,031,893; 4,394,863; 4,484,910; 4,640,686; 4,678,461; 4,795,433; 4,832,682; 5,085,641; 5,092,843; 5,102,393; 5,354,286; 7,449,012; and 8,048,035, all of which are hereby incorporated by reference in their entireties for all purposes.

Medicament device 100 or packaging 160 may be imprinted with various medicament information. For example, medicament device 100 may include the name of the medicament, active ingredients, dosage, expiration date, lot ID, and product serialization number. The medicament information may be printed in a manner that is machine-readable. For example, the medicament information may be printed as a quick response (QR) code 170. The medicament information may also be printed as text that is easily recognized using optical character recognition (OCR). Packaging 160 may include a container such as a box or tube as well as any inserts or cards included within the packaging. It should be apparent that any information included on the medicament device 100 may instead be located on packaging 150. As will be discussed in further detail below, the medicament information may also be digitally encoded in a memory 130 of the medicament device.

The electronic medicament device 100 may further include sensor 110, ID tag 120, memory 130, display 140, and speaker 150. Although not illustrated, the electronic medicament device may include additional hardware such as, for example, a processor and/or additional communication interfaces. A processor may interconnect one or more of those components illustrated in FIG. 1. Such additional communication interface may include, for example, an interface for communication via wifi, a mobile carrier network, or satellite. Alternatively, the additional communication interface may include a wired communication interface.

Sensor 110 may detect activation of electronic medicament device 100. Sensor 110 may include a frangible element that completes or breaks an electronic circuit when electronic medicament device 100 is activated. Sensor 110 may provide a signal to ID tag 120 to perform an action in response to use of the medicament. Sensor 110 may alter memory 130 to indicate that the medicament device 100 is used and may log a time of use.

In various embodiments sensor 110 may include a temperature sensor. The temperature sensor may continuously measure the current temperature of the medication. The temperature sensor may provide the current temperature to a processor to compare to approved temperatures. In embodiments where the medication is epinephrine, the approved temperature range may be 15-30° C. An alarm may be generated by display 140 or speaker 150 if the current temperature is outside of the approved temperature range.

In various embodiments, sensor 110 may include a colorimetric sensor capable of determining the color of the medicament. For example, sensor 110 may be a spectrophotometer. The color of the medicament may be indicative of the quality of the medicament. For example, a medicament may turn from clear to pink or brown if the medicament becomes degraded.

ID tag 120 may include an RFID, NFC, or other tag for short range wireless communications. Such tags may be powered by passive energy and not require a battery. In various embodiments, ID tag 120 may include a battery powered wireless transmitter using, for example, Bluetooth. ID tag 120 may provide information from electronic medicament device 100 to a wireless reader such as, for example, wireless reader 140 or a NFC enabled mobile device. ID tag 120 may be connected to or include memory 130. In various embodiments, ID tag 120 may be located on packaging 160 rather than medicament device 100.

Memory 130 may store information regarding electronic medicament device 100. Memory 130 may include a non-volatile memory such as a read-only memory (ROM) or an electronically erasable programmable read only memory (EEPROM). Information stored by memory 130 may include manufacture date, expiration date, medication, dose size, audio instructions, text instructions, other instructions, prescription information, re-order information, and emergency contact information.

Display 140 may include a display such as a LCD, LED array, or a single LED. Display 140 may display information about electronic medicament device 100. Display 140 may read and display any information stored in memory 130. For example, display 140 may display the expiration date of the medication. Display 140 may also display instructions for a user. In various embodiments, display 140 may illuminate, flash, or display a particular message in response to particular events such as the expiration of the medication, use of the medicament, or separation from another device such as case or a mobile device 220.

Speaker 150 may provide audio output. For example, speaker 150 may play pre-recorded instructions stored in memory 130. In various embodiments, ID tag 120 or another communication interface (not shown) may download or stream information from another device to be played by speaker 150. For example, the electronic medicament device 100 may stream information from an application server 250 or from a remote operator, either directly or via a mobile device 220

In various embodiments, the electronic medicament device 100 may be reusable. As such, the electronic medicament device 100 may receive a disposable cartridge or component set including the medication and/or a clean needle. Such cartridge or component set may include its own RFID tag or other means for communicating an expiration date or other information to the electronic medicament device 100 or mobile device 220.

In various embodiments, the processor or other component of the electronic medicament device 100 may alter the operation of the electronic medicament device 100 based on user information or other information. For example, the electronic medicament device 100 may provide different dosages based on a dosage prescribed to an authorized user. As another example, a user may input a patient weight, height, and/or body mass index (BMI) into a keypad of the electronic medicament device 100 or input information into a mobile device 220 and wirelessly transmit the user information to the medicament device 100. The processor may then calculate and administer an appropriate dosage based on the input factors. As another example, the processor may prevent or disable medicine administration when the user is not authorized for such administration.

Figure 2:
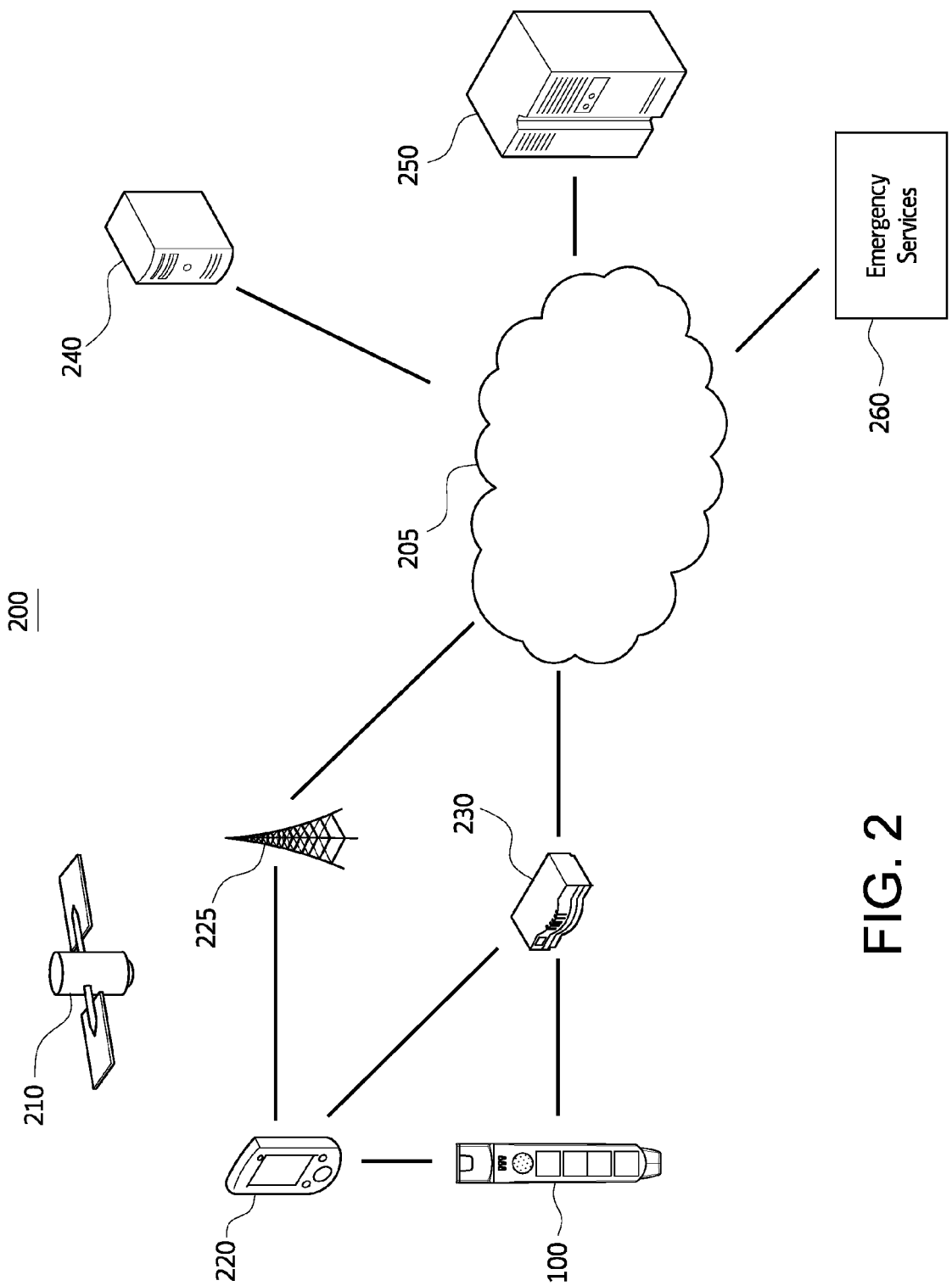
FIG. 2 illustrates an exemplary network environment for an electronic medicament device.

FIG. 2 illustrates an exemplary network environment 200 for electronic medicament device 100. Electronic medicament device 100 may interact with various elements of network environment 200 to provide emergency access and enhanced features. Network environment 200 may include network 205, GPS satellites 210, mobile device 220, mobile base station 225, wireless router 230, medical server 240, central control 250, and emergency services 260.

Network 205 may be a digital network for communicating information. For example, network 205 may be the Internet. Network 205 may transmit information between various end users and devices. Network 205 may also include telephone networks.

GPS satellites 210 may enable electronic medicament device 100, mobile device 220, and other devices to determine their respective physical locations. GPS satellites 210 may be geosynchronous satellites that broadcast signals. GPS enabled devices may use the signals from multiple satellites to determine their location. In various embodiments, GPS satellites 210 may include or be replaced by terrestrial location systems. For example, wi-fi access points may be used to detect the physical location of a device.

Mobile device 220 may be a device such as a smart phone, tablet computer, laptop, or any other computing device capable of executing applications and performing communication. In various embodiments, mobile device 220 is an NFC enabled mobile phone that can communicate using short range wireless protocols as well as local networking and mobile networks. In particular, mobile device 220 may communicate with a mobile network using mobile base station 225. Mobile device 220 may include location detecting services such as GPS.

Mobile device 220 may interact with the electronic medicament device 100 using RFID, NFC, or other wireless communication. Mobile device 220 may read medicament information that is either printed on medicament device 100 or stored in memory 130. For example, mobile device 220 may include a camera and application configured to read a QR code or printed text. Mobile device 220 may also read data from the memory 130 using a short-range wireless protocol such as RFID, NFC or Bluetooth. The short-range wireless communication may also be used by mobile device 220 to determine the presence of a medicament device 100. For example, mobile device 220 may periodically attempt to read the medicament device 100 and determine that the medicament device 100 is not present if the mobile device 220 is unable to read the medicament device 100.

Mobile device 220 may include an application specifically for interacting with electronic medicament device 100. Mobile device 220 may access memory 130 via ID tag 120 and read or write data. Mobile device 220 may detect changes in electronic medicament device 100 and perform actions in response. For example, mobile device 220 may detect that electronic medicament device 100 has been activated. Mobile device 220 may automatically contact emergency services 260 and allow a user to speak with emergency personnel, or mobile device 220 may provide a pre-recorded message to emergency services 260 indicating that the medicament has been activated to treat a condition of the patient. Mobile device 220 may also provide a location based on GPS information so that emergency personnel can locate the patient. The application may also interact with server 250 to provide additional medicament related information and services. For example, the application may provide disease information and news, medicament registration, reminders, product accessory information, medicament insert and patient information, and local allergy information.

ID tag 120 may be used to determine whether electronic medicament device 100 is within close proximity to a mobile device 220. ID tag 120 may periodically poll or be polled by a wireless reader in the mobile device 220. If the poll does not occur when expected, or the mobile device does not respond, electronic medicament device 100 may generate an alert. For example, electronic medicament device 100 may play a sound through the speaker 150 or flash the display 140 to alert a user. The alert may remind the user to keep the medicament close by in case of emergency. Mobile device 220 may also generate an alert if electronic medicament device 100 is not detected. Mobile device 220 may be configured to check for the presence of electronic medicament device 100 whenever the user enters or leaves a particular location. For example, mobile device 220 may generate an alert if a user leaves home without the electronic medicament device.

In various embodiments, the ID tag 120 may be used to actively search for electronic medicament device 100. Mobile device 220 may be configured to transmit a signal to ID tag 120 upon activation by a user. The signal may be received by ID tag 120 and cause the speaker 150 to produce an audible sound. The volume or pitch of the sound may vary depending on the strength of the received signal. Alternatively, mobile device 220 may detect a signal reflected by an ID tag 120 such as a passive RFID tag. Mobile device 220 may play an audible sound and vary the volume or pitch depending on the strength of the reflected signal.

Mobile device 220 may also contact emergency contacts. For example, mobile device 220 may email, message, or call any emergency contacts stored in memory 130 or within mobile device 220 when the electronic medicament device 100 is used or generates some other alert. Mobile device 220 may select contacts based on time of day or other available information.

Upon detection of an expired medicament or activation of the medicament, mobile device 220 may initiate ordering a replacement medicament Mobile device 220 may send an order to either control center 250 or medical server 240. The order may include patient and prescription information. Medical server 240 may determine whether the prescription includes refills, whether replacements are allowed without a prescription, or whether the patient has a valid or perpetual prescription for the medicament. Medical server 240 may automatically fulfill the order if the prescription is authorized. Alternatively, medical server 240 may schedule an appointment with the patient's doctor for a new prescription and to follow-up regarding the deployment of the medicament.

Wireless router 230 may be a wireless router providing connectivity to a local area network (LAN) and the Internet. Wireless router 220 may be accessed electronic medicament device 100, and mobile device 220. Accordingly, wireless router 220 may provide these devices with Internet access to send and receive data.

Medical server 240 may be a server operated by a health care provider, health insurance provider, or government health agency. Medical server 240 may store patient information. Medical server 240 may provide patient information to authorized devices such as the patient's mobile device 220, control center 250, and emergency services 260. Medical server 240 may be configured to receive and process particular messages from electronic medicament device 100, mobile device 220, and control center 250. For example, medical server 240 may be configured to verify prescriptions and order refills.

Application server 250 may be a computer server operated by a medicament manufacturer or other third party. The application server 250 may provide a downloadable application for execution on a mobile device. The application server 250 may also provide support for the downloadable application and/or a web application. The application server 250 may include a database of registered medicament information provided by patients who opt to register the medicament device 100. The application server 250 may provide various services accessible via the application. The application server 250 may provide audio and/or video instructions that may be downloaded or streamed to a mobile device. The application server 250 may provide information to a mobile device based on a registered medicament device. For example, the application server 250 may track expiration dates and provide notification of approaching expiration dates. In various embodiments, the application server 250 may provide a tracking system enabling a registered user to track the last known physical location of registered medicament devices.

The electronic medicament device 100 may provide usage information to the application server 250 which, in turn, may process the data for various uses. For example, the application server 250 may provide the processed usage data to an application executing on a mobile device, such as mobile device 220. Such application may provide, for example a map indicating where the user has administered the electronic medicament device 100 and/or other electronic medicament devices 100. Such application could also present a real-time alert as to when the electronic medicament device 100 has been used, including location information. The application may also provide historical data and analysis of electronic medicament device 100 usage events such as event listings and graphs. As another example, the application server 250 may track disposal and/or recycling of medicament device 100. A disposal or recycling facility may scan medicament information including a lot ID and product serialization number from medicament device 100. The disposal or recycling facility may send the scanned medicament information to application server 250 and/or medical server 240 for reconciliation with registered medicament device 100.

Figure 3:
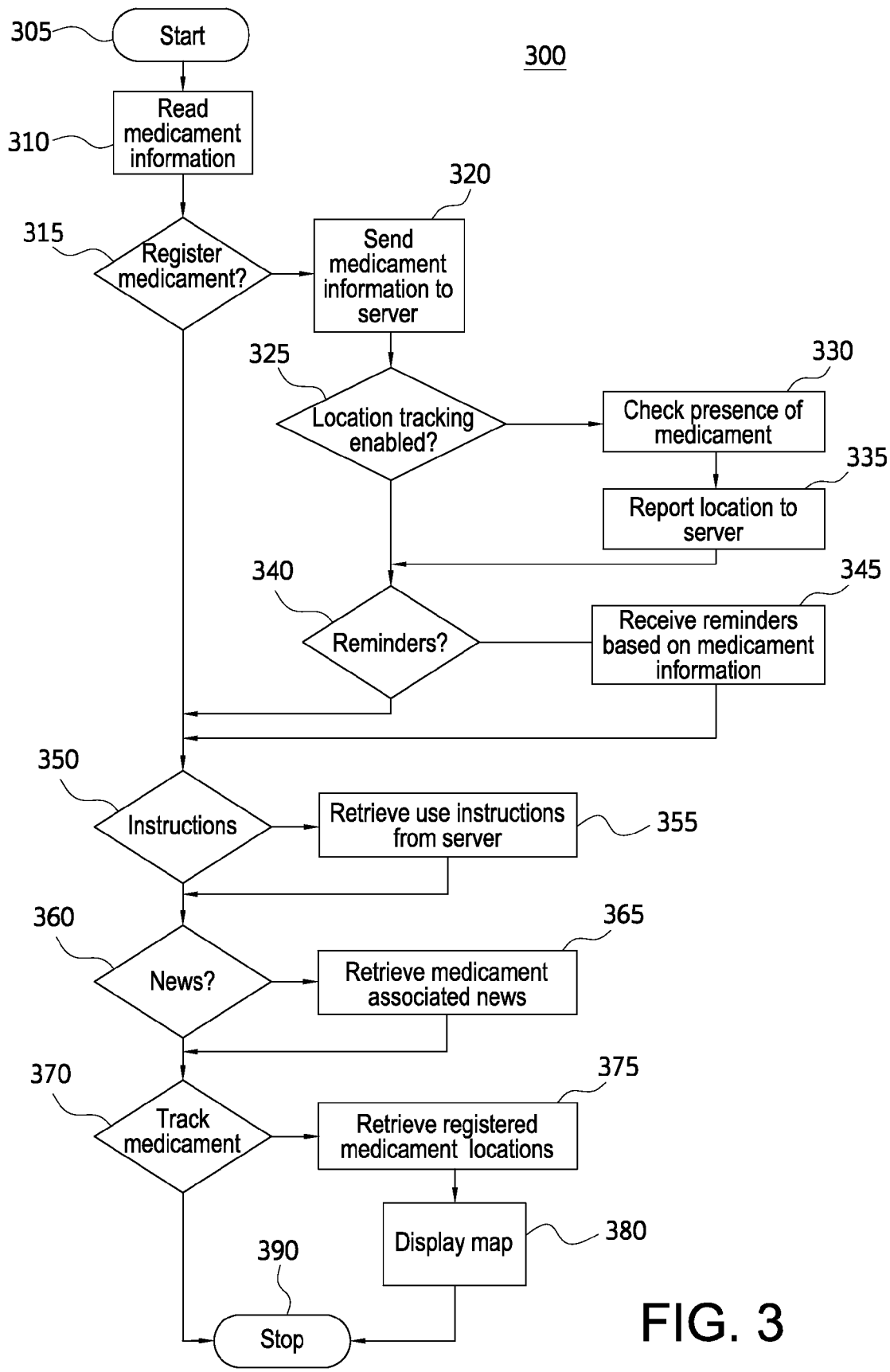
FIG. 3 illustrates a flowchart showing an exemplary method performed by a mobile device.

FIG. 3 illustrates a flowchart showing an exemplary method 300 performed by a mobile device 220. Mobile device 220 may include an application configured to cause the processor and other components of mobile device 220 to perform the steps of the method 300. The method 300 may begin at step 305 and proceed to step 310.

In step 310, the mobile device 220 may read medicament information from the medicament device 100. In various embodiments, the mobile device 220 may use a camera take a picture of medicament device 100 or the packaging thereof. For example, a user may take a photograph of the expiration date, lot number, and serialization number, or take a photograph of a QR code. The mobile device 220 may analyze the photograph to determine medicament information. The mobile device 220 may also forward the photograph to an application server 250 for analysis. In various embodiments, the mobile device 220 may read the medicament information from the memory 130.

In step 315, the mobile device 220 may determine whether a user wishes to register the medicament device 100. The mobile device 220 may present a user interface providing an explanation of the benefits of registration an option to register. The user interface may also provide the ability for the user to enter contact information or to manually enter medicament information. If the user chooses to register the medicament device 100, the method 300 may proceed to step 320. If the user chooses not to register the medicament device 100, the method 300 may proceed to step 350.

In step 320, the mobile device 220 may send medicament information to the server. The mobile device 220 may send medicament information read from the medicament device 100, packaging, and/or memory 130. The mobile device 220 may also send user information entered by the user. In various embodiments, the user may update an existing registration with a new medicament device 100. Accordingly, the server 150 may already have user information and only a user identifier may be sent with the medicament information. In various embodiments, the mobile device 220 may send the medicament information to medical server 240 in addition to application server 250. For example, a government health agency may collect medicament information. Application server 250 may also forward the medicament information to medical server 240.

In step 325, the mobile device 220 may determine whether the user wishes to register for a location tracking service. As will be described in further detail below, the location tracking service may monitor the location of the medicament device 100 and help a user find the device 100 if it is lost or activated. The mobile device 220 may prompt a user to enter additional information useful for tracking the location of the medicament device 100 such as a phone number of an additional mobile device 220 that may be used to track the medicament device 100. The additional mobile device 220 may be, for example, a mobile device usually carried by a child who has been prescribed the medicament device 100. If the user enables location tracking, the method 300 may proceed to step 330. If the user opts out of location tracking, the method 300 may proceed to step 340.

In step 330, the mobile device 220 may check for the presence of the medicament device. In various embodiments, the mobile device 220 may use a short-range wireless communication protocol such as Bluetooth to poll the medicament device. If the medicament device 100 is present, the mobile device 220 may establish a connection with the medicament device 100 and receive additional information.

In step 335, the mobile device 220 may report the location of the medicament device 100 to the server 150. If the mobile device 220 detected the presence of the medicament device 100 in step 330, the mobile device may report the location of the mobile device 220 as the location of the medicament device 100. If the medicament device 100 is not detected, the mobile device 220 may report a missing medicament device having no known location or report the last known location of the medicament device 100.

In step 340, the mobile device 220 may determine whether a user wishes to receive reminders regarding the medicament device 220. The mobile device 220 may present a user interface displaying information regarding available reminders. The user of the mobile device may select those reminders he or she would like to receive. Exemplary reminders regarding a medicament device may include a reminder to replace an expired medicament device, a reminder to review instructions, a reminder to obtain a new prescription, a reminder to perform a medical test, and a reminder to take a periodic dose from the medicament device. The mobile device 220 may send the selected reminders to server 150, which may monitor for events related to the reminders. In step 345, the mobile device 220 may receive a reminder from the server 150 based on medicament information. In various embodiments, the reminder may be received via simple messaging service (SMS), email, or an application based messaging system.

In step 350, the mobile device 220 may determine whether the user wishes to receive instructions. The user may indicate a desire to receive instructions by selecting a button within the application. In various embodiments, the mobile device 220 may automatically request instructions based on the user scanning a QR code or taking a picture of the medicament device. If the user desires to receive instructions, the method 300 may proceed to step 355. If the user does not desire to receive instructions, the method 300 may proceed to step 360. In step 355, the mobile device 220 may request the instructions from the server 250. The request may include information identifying the medicament device 100. In various embodiments, the request may include only a name or identifier of the medicament device 100 and not particular information such as a lot number, product serialization number, or expiration date. In step 355, the mobile device 220 may receive instructions from server 250. The instructions may be in the form of a video streamed from the application server 240. The instructions may also include audio or written instructions.

In step 360, the mobile device 220 may determine whether the user wishes to receive news regarding the medicament device 100. The user may indicate a desire to receive news by selecting a button within the application. If the user desires to receive news, the method 300 may proceed to step 365. If the user does not desire to receive news, the method 300 may proceed to step 370. In step 365, the mobile device 220 may receive news updates from the server 250. The news updates may be pushed to the mobile device 220 based on the identified medicament device.

In step 370, the mobile device 220 may determine whether the user desires to track a medicament device 100. The tracking service may require registration of the medicament device with server 250. The user may indicate a desire to track a medicament device by selecting a button within the application. In various embodiments, tracking a medicament device 100 may be initiated by an application server 250 in response to an event concerning the device. For example, use of a registered medicament device 100 may be reported to the application server 250 by a patient's mobile device. The application server 250 may then push a notification to another user device 220, such as a device of a parent or other emergency contact, and provide tracking information. If the user desires to track a medicament device 100, the method 300 may proceed to step 375. If the user does not desire to track a medicament device, the method 300 may proceed to step 390, where the method 300 ends.

In step 375, the mobile device 220 may retrieve information regarding registered medicament devices 100 including location information. The mobile device 220 may require the user to enter a password or perform other security operations to ensure only the registered user has access to the medicament device information. The mobile device 220 may present a list of medicament devices 100 registered to the user or may request information regarding all registered medicament devices. The application server 250 may receive the request and extract medicament device information from a database. The application server 250 may also attempt to update the medicament device locations by polling other mobile devices associated with registered medicament devices for current medicament device information.

The mobile device 220 may receive the medicament information from the server 250. The medicament information may include a location, which may be, for example, longitude and latitude coordinates or a street address. The medicament information may also include information such as the current temperature of the medicament device, the time of the last use of the medicament device, and a number of doses remaining in the medicament device. In step 380, the mobile device 220 may present the medicament device information to the user as a map. The map may indicate the current location of the medicament device 100 as well as the current location of the mobile device 220. It will be apparent that in various embodiments, the exemplary method 300 may be implemented as multiple independent methods 300 may be implemented as multiple independent methods. For example, steps 310-345 may be implemented as a registration method while steps 350-380 may be implemented as a separate operation method. Additional implementation details and modifications will be apparent.

Figure 4:
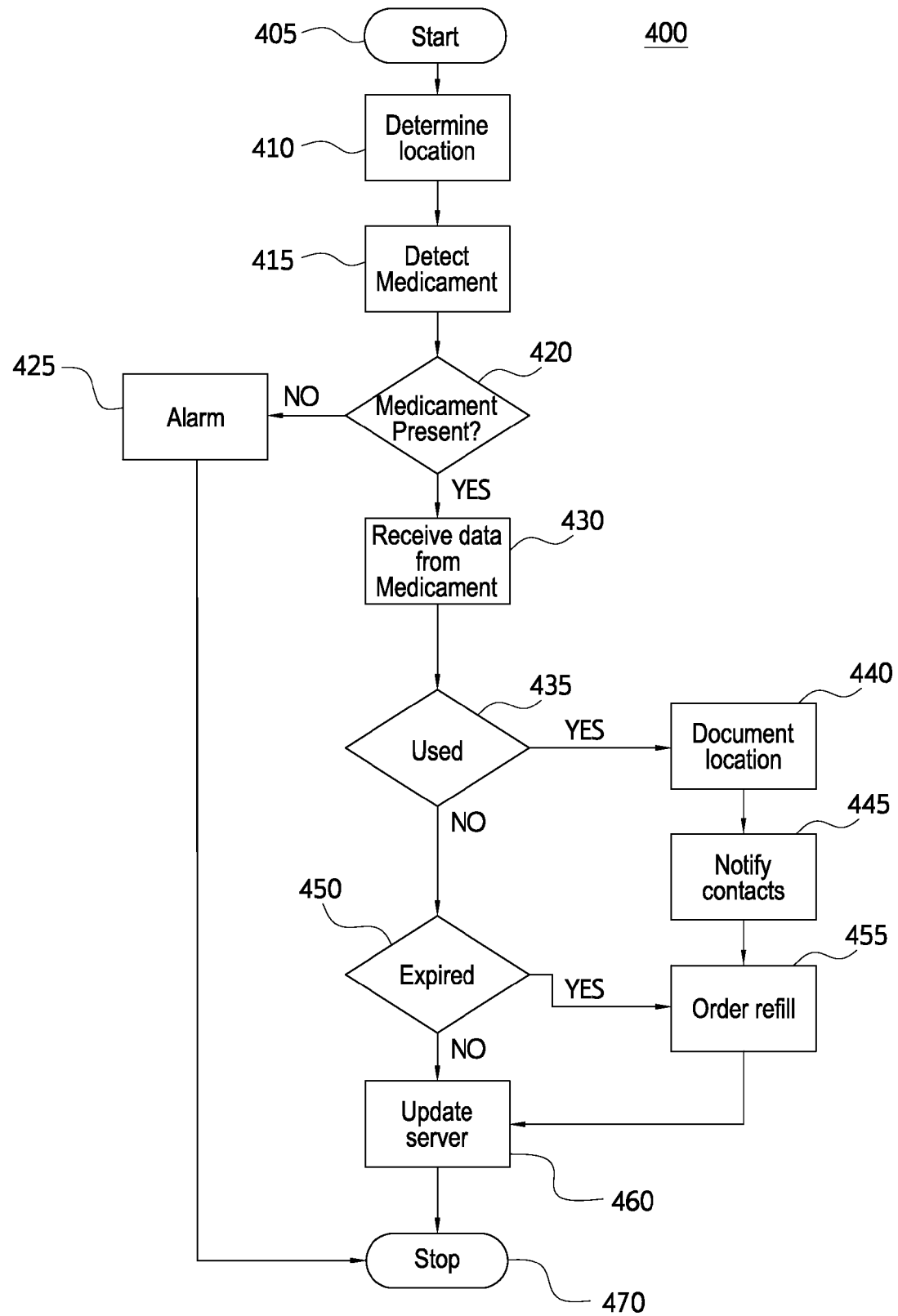
FIG. 4 illustrates a flowchart showing an exemplary method of monitoring a medicament.

FIG. 4 illustrates a flowchart showing an exemplary method 400 of monitoring a medicament. The method 400 may be performed by a mobile device 220 in communication with an electronic medicament device 100. The method 400 may be performed as step 330 of method 300 illustrated in FIG. 3.

The method 400 may begin at step 405 and proceed to step 410. In step 410, the mobile device 220 may determine its location. In various embodiments, mobile device 220 may use the location to determine whether to proceed with the method. For example, the mobile device 220 may discontinue the method if the mobile device is in a designated location, or the mobile device may delay the method until a change in location is detected.

In step 415, the mobile device 220 may detect any electronic medicament devices nearby. Mobile device 220 may use RFID, NFC, Bluetooth or another close range protocol to poll nearby tags 120 on a medicament device. Mobile device 220 may be configured to poll one or more specific electronic medicament devices with identifiers known by mobile device 220. In step 420, mobile device 220 may determine whether an electronic medicament device 100 is present. If no medicament device is present, the method may proceed to step 425. If a medicament device is detected, the method may proceed to step 430.

In step 425, the mobile device 220 may generate an alarm. The alarm may indicate any particular medicament device that was not detected. The alarm may include a message identifying the medicament device by name or by a condition that it treats. If the mobile device performs method 400 frequently, it may be likely that the medicament device is nearby, although out of range of the short range wireless protocol. Accordingly, a user may be reminded to retrieve the medicament device. The mobile device 220 may also generate a message to another mobile device. For example, the mobile device 220 may send an SMS message or email to a parent, guardian, or other emergency contact indicating that the medicament device 100 has been separated from the mobile device 220. The method 400 may then proceed to step 460, where the method ends.

In step 430, the mobile device 220 may receive data from the medicament device. Mobile device 220 may send a read command to read data from memory 130. In various embodiments, mobile device 220 may receive data from the electronic medicament device 100 when sensor 110 determines that the device 100 has been activated. In step 435, mobile device 220 may determine whether the medicament device 100 has been used. Mobile device 220 may determine the status of sensor 110 or parse data received in step 430. If the medicament device has been used, the method may proceed to step 440. If the medicament device has not been used, the method may proceed to step 450.

In step 440, mobile device 220 may document the current location of the mobile device. The location of the mobile device may be used to identify the location of device usage. In step 445, the mobile device may notify emergency contacts. Mobile device 220 may contact emergency services, for example, by dialing 911. The mobile device 220 may turn on a speaker phone to allow a user, who may be suffering from anaphylaxis or another medical condition to speak to an emergency dispatcher. If mobile device 220 does not receive any voice input, mobile device 220 may play a recorded message indicating that the electronic medicament device has been activated at the stored location. Mobile device 220 may also contact other people. For example, mobile device 220 may call, email, or message emergency contacts stored in mobile device 220 or memory 130.

In step 450, mobile device 220 may determine whether the electronic medicament device 100 is expired. Mobile device 220 may compare an expiration date received from the electronic medicament device 100 to the current date. In various embodiments, the mobile device 220 may also have the ability to read the quality of the medicament. For example, mobile device 220 may read information from a sensor 110 in medicament device 100. The sensor 110 may determine that the medicament has expired early if, for example, the medicament device 100 was stored at an inappropriate temperature or has changed properties such as colors. In various embodiments, the mobile device 220 may be able to determine the quality of the product. For example, the camera of the mobile device may act as a spectrophotometer to measure the color of the medicament. Alternatively, the mobile device 220 may transmit a picture of the medicament device to application server 250 for spectrophotometric analysis. The medicament device 100 may include a transparent window and colored markings to assist with the spectrophotometric analysis. The mobile device 220 may determine that the medicament has expired early if the medicament exhibits a certain property. If the medicament device is expired, the method may proceed to step 455. If the medicament device is not expired, the method may proceed to step 450.

In step 455, the mobile device 455 may initiate an order for a refill or replacement electronic medicament device. Mobile device 220 may send an order to control center 250 and/or medical server 240. The method may then proceed to step 460.

In step 460, the mobile device 220 may update an application server 250 with information regarding the medicament device 220. The application server 250 may use the updated information to provide up to date information to other users associated with a registered medicament device. For example, the updated information may be used to provide the tracking service described above. The updated information may also be used by the application server 250 to generate notifications regarding local conditions such as allergy and asthma alerts. The application server 250 may provide such alerts as news to users who have registered medicament devices for treating the same condition. The method may proceed to step 470, where the method may end.

Figure 5:
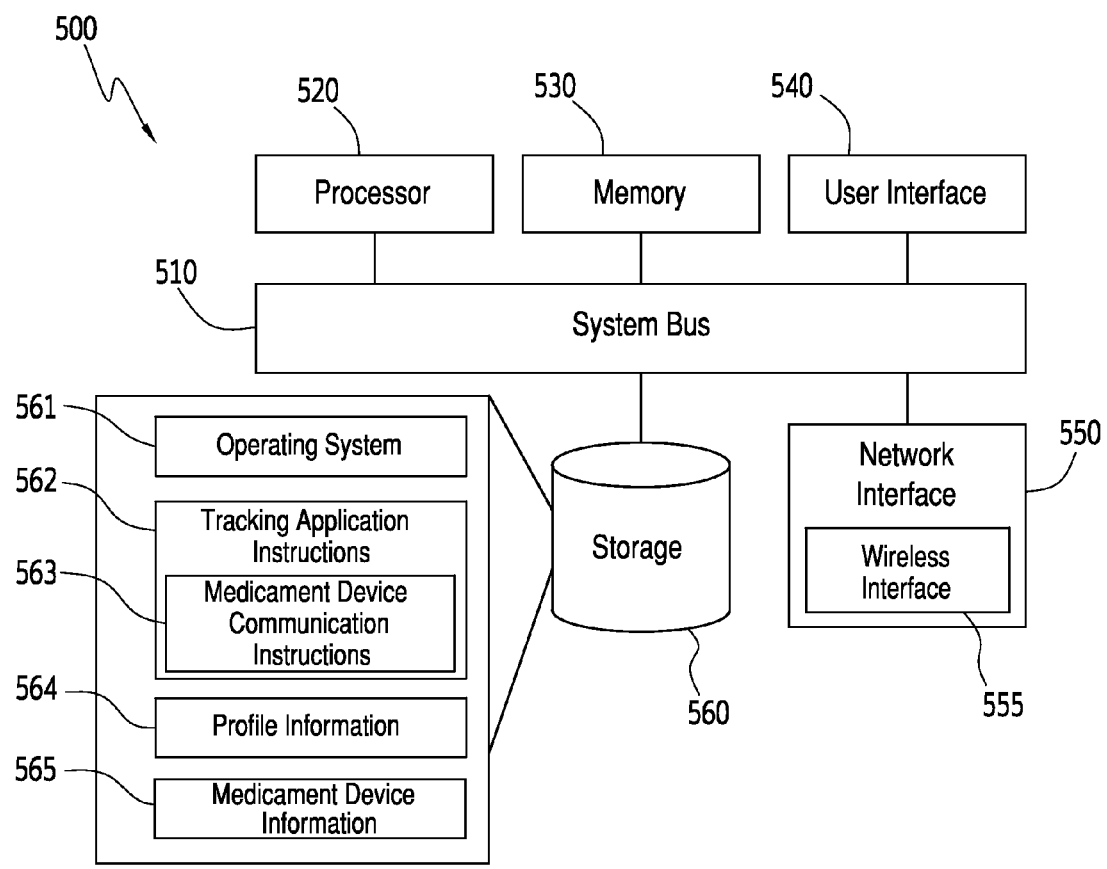
FIG. 5 illustrates an exemplary hardware system for executing a medicament device tracking application.

FIG. 5 illustrates an exemplary hardware system 500 for executing a medicament device tracking application. The exemplary device 500 may correspond to the mobile device 220 of FIG. 2. As shown, the device 500 includes a processor 520, memory 530, user interface 540, network interface 550, and storage 560 interconnected via one or more system buses 510. It will be understood that FIG. 5 constitutes, in some respects, an abstraction and that the actual organization of the components of the device 500 may be more complex than illustrated.

The processor 520 may be any hardware device capable of executing instructions stored in the memory 530 or the storage 560. As such, the processor may include a microprocessor, field programmable gate array (FPGA), application-specific integrated circuit (ASIC), or other similar devices.

The memory 530 may include various memories such as, for example L1, L2, or L3 cache or system memory. As such, the memory 530 may include static random access memory (SRAM), dynamic RAM (DRAM), flash memory, read only memory (ROM), or other similar memory devices.

The user interface 540 may include various hardware for enabling interaction with a user of the device 500. For example, the user interface 540 may include a touch screen display, a speaker, and a microphone. In some embodiments, the user interface 540 may include a monitor, a keyboard, and a mouse. Various alternative sets of user input/output hardware will be apparent.

The network interface 550 may include one or more devices for enabling communication with other hardware devices. The network interface 550 may also include one or more wireless interfaces 555 to enable such communications via a wireless communications medium. For example, the wireless interface 550 may include one or more antennae, reception circuitry capable of signal demodulation according to various schemes, transmission circuitry capable of signal modulation according to various schemes, and one or more protocol stacks. The wireless interface 555 may provide for communication according to one or more wireless protocols such as, for example, WiFi, 3G, 4G, NFC, RFID, or Bluetooth. Such communication may occur directly between the hardware 500 and another device such as a medicament device, or may occur via a network of intermediate devices such as the Internet.

The storage 560 may include one or more machine-readable storage media such as read-only memory (ROM), random-access memory (RAM), magnetic disk storage media, optical storage media, flash-memory devices, or similar storage media.

For example, the storage 560 may store operating system instructions 561 for providing various basic functionalities to the system 500 and applications executing on the system. As an example of operating system functionality, the operating system instructions may provide basic input and output functions for outputting various types of alerts such as audible alarms and visual alarms. In some embodiments, the operating system may provide a notification bar or other element for outputting notifications that is always visible while the display of the device 500 is activated and provides icons or other notifications associated with various different applications.

The storage 560 may also store tracking application instructions 562 for providing a medicament tracking application. In particular, the tracking application instructions 562 may implement any combination of the functionalities described herein with respect to various medicament devices or mobile devices. For example, the tracking application instructions may be configured to output various alarms to a user of the device 500 based on events such as medicament expiration, device activation, or a missing device. Various other functionalities for the tracking application instructions will be apparent in view of the foregoing. To facilitate various functionalities, the tracking application instructions 562 may also include, in some embodiments, medicament device communication instructions 563 for providing various forms of communication between the device 500 and one or more medicament devices. For example, the medicament device communication instructions 563 may enable optically reading expiration or other information from a medicament device or packaging, wirelessly reading such information from a medicament device or packaging, polling for the proximity of a medicament device or packaging, or receiving location information or other information from the medicament device or packaging via a network such as the Internet. Various other forms of communication with a medicament device or packaging will be apparent.

The storage 560 may also store various data for use by the tracking application instructions 562. For example, the storage 560 may store profile information 564 for various registered individuals. The profile information 564 may include information such as name, allergies, prescribed medicament devices, or emergency contact information. The storage 560 may also store medicament device information 565 such as, for example, device identifiers, associated profiles, expiration date, or location information.

It will be apparent that various information described as stored in the storage 560 may be additionally or alternatively stored in the memory 530. In this respect, the memory 530 may also be considered to constitute a "storage device." Various other arrangements will be apparent. Further, the memory 530 and storage 560 may both be considered to be "non-transitory machine-readable media." As used herein, the term "non-transitory" will be understood to exclude transitory signals but to include all forms of storage, including both volatile and non-volatile memories.

While the device 500 is shown as including one of each described component, the various components may be duplicated in various embodiments. For example, the processor 520 may include multiple microprocessors that are configured to independently execute the methods described herein or are configured to perform steps or subroutines of the methods described herein such that the multiple processors cooperate to achieve the functionality described herein.

FIG. 6 illustrates a first exemplary user interface 600 for a medicament device tracking application. The user interface 600 may be displayed, for example, by a mobile device after opening the medicament tracking application. As shown, the user interface 600 includes an operating system-provided notifications bar 605 for displaying various information such as, for example, a current time, signal strength, battery charge, carrier, and application-generated alarms or other notifications. The user interface 600 also includes an application navigation bar 610 for enabling quick navigation through the tracking application. For example, as shown, the home button on the navigation bar 610 is highlighted, indicating the user interface 600 is displaying a portion of the "home" area of the application. As such, the user interface 600 also includes a main navigation menu 620 including various buttons for accessing different features of the application. For example, a "Track My Auto-Injectors" button may provide quick access to a tracking interface, an example of which will be described in greater detail below with respect to FIG. 13. As another example, a "Notify My Contact" button may be selected to initiate a phone call or other form of communication with a person previously stored as an emergency contact for the user. Various other buttons for inclusion in the navigation menu 620 will be apparent.

FIG. 7 illustrates a second exemplary user interface 700 for a medicament device tracking application. The user interface 700 may correspond to a "learning" area of the application, as indicated by the highlighting of the "Learn" button on the navigation bar 610. As shown, the user interface 700 provides an important safety information window 720 for conveying information to the user. Upon selection, the safety information window 720 may expand to provide additional area for viewing the information. The user interface 700 also includes a learning navigation menu 730 for accessing various areas of the "learning" area. For example, each of the buttons in the menu 730 may lead to one or more pages of a requested type of content.

FIG. 8 illustrates a third exemplary user interface 800 for a medicament device tracking application. The user interface may correspond to a "how to" area of the application, as indicated by the highlighting of the "How To" button on the navigation bar 610. As shown, the important information pane 720 is displayed on this user interface as well. The user interface 800 also includes a pane 830 for conveying information about how to use the associated medicament device. The pane 830 may also include one or more embedded videos 835 for instructing a user in administration of a medicament device.

FIG. 9 illustrates a fourth exemplary user interface 900 for a medicament device tracking application. The user interface may correspond to a "tracking" area of the application, as indicated by the highlighting of the "Track" button on the navigation bar 610. In addition to the important information pane 720, the user interface 900 includes a top pane with buttons 930, 935 leading to different "tracking" functionalities of the application. For example, the pane may include an "allergen profiles" button 930 for reviewing, updating, and sharing allergen information for various patients registered with the application. As another example, the pane may include a "track your auto-injectors" button 935 for determining a location or other status of auto-injector type medicament devices registered with the application. In some embodiments, patient profiles or medicament devices are registered with the application before tracking is enabled.

Figures 10, 11:
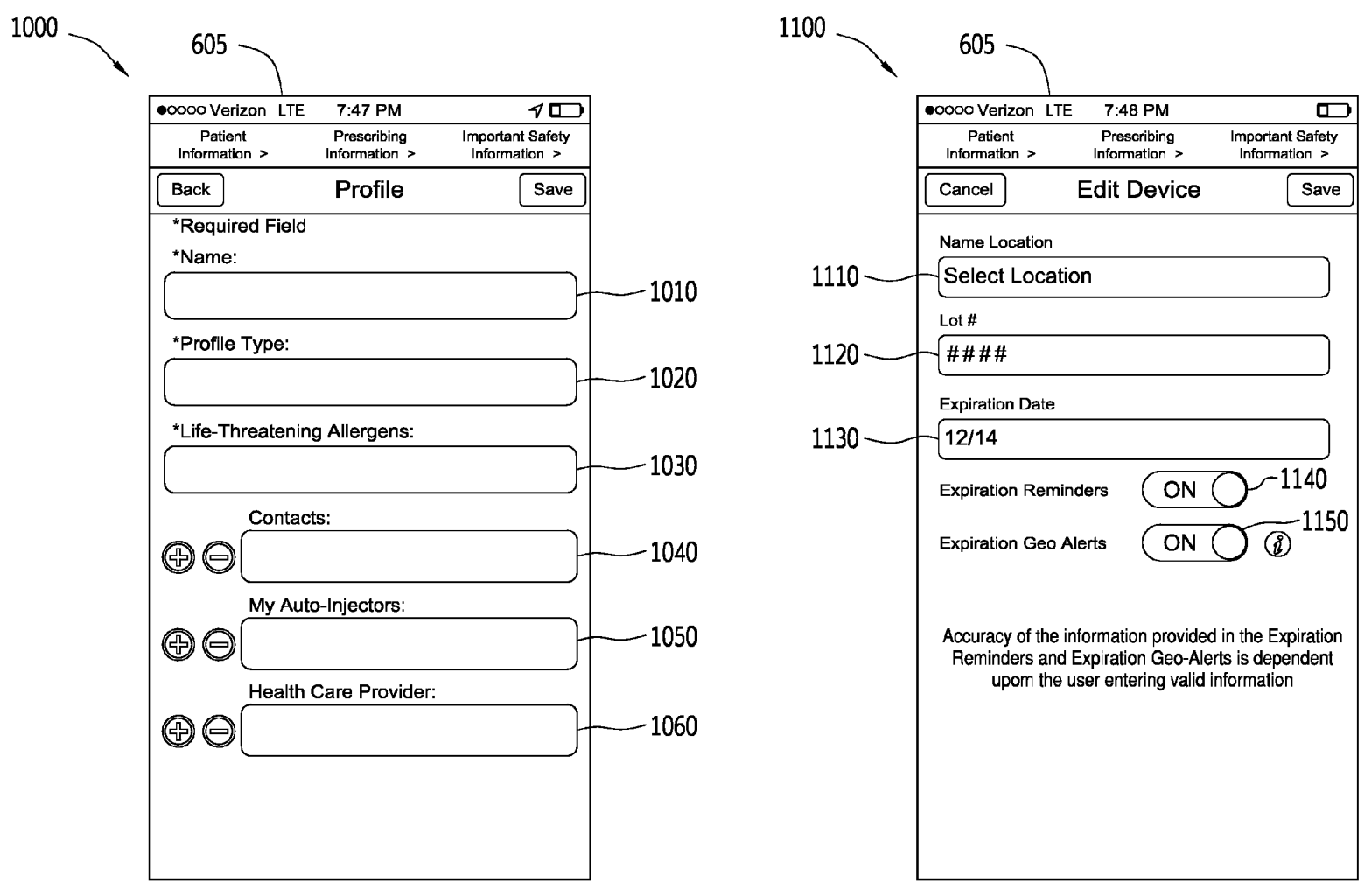

FIG. 10 illustrates a fifth exemplary user interface 1000 for a medicament device tracking application. The user interface 1000 may be an interface for registering a new patient profile with the application. As shown, the user interface provides various fields for entering profile information. A name field 1010 receives a name for the patient. A profile type field 1020 receives an identification of the type of profile being registered. For example, in some embodiments, the profile type field 1020 receives a selection from a group of values such as, for example, "self," "spouse," "child," "family member," "friend," or "other." An allergens field 1030 receives a list of allergens associated with the profile. For example, in some embodiments, the profile type field 1020 receives a selection of one or more items from a group of values such as, for example, "Eggs," "Fish," "Milk," "Peanuts," "Honey Bees," "Hornets," "Some Fire Ants," "Aspirin," "Ibuprofen," "Exercise," "Latex," or "Other Life-Threatening Allergens." Various additional allergens for inclusion in the list will be apparent to those of ordinary skill in the art.

A contacts field 1040 receives a selection of one or more emergency contacts. This list may be used when the application is used to communicate with an emergency contact such as, for example, after selection of the "Notify My Contact" button on user interface 600. In various embodiments, the user may manually enter each contact into the field 1040, including a name and phone number. In some embodiments, the user may select for inclusion in the field 1040 one or more contacts provided by an address book or other contact list of the phone operating system or other application.

An auto-injectors field 1050 receives one or more auto-injectors prescribed to the patient and to be tracked by the application. An exemplary interface for registering a new auto-injector or other medicament device will be described in greater detail with respect to FIG. 11. A health care provider field 1060 receives one or more identifications of health care providers. This list may be used when the application contacts such health care providers such as, for example, during a user-indicated emergency or upon the user indicating a desire to schedule an appointment for a prescription of a new medicament device (e.g., due to use or expiration of another medicament device). The health care provider information 1060 may be entered manually or imported from the phone operating system or another application.

FIG. 11 illustrates a sixth exemplary user interface 1100 for a medicament device tracking application. The user interface 1100 may be an interface for registering a new medicament device to be tracked by the application. A location field 1110 may receive an indication of a location of the medicament device. An exemplary interface for entering location information will be described with respect to FIG. 12 below. A lot number field 1120 may receive an indication of the lot number associated with the medicament device while the expiration date field 1130 may receive an indication of the expiration data associated with the medicament device. An expiration reminders button 1140 receives a selection of whether the user wishes to receive reminders regarding expiration events for the newly medicament device generally. Similarly, an expiration geo alerts button 1150 receives a selection of whether the user wishes to receive reminders regarding expiration events for nearby medicament devices. For example, in various embodiments, the application may provide special "geo alerts" whenever the mobile device is within a predetermined distance (e.g., one mile) from the location of an expired or expiring medicament device.

As shown, the interface 1100 receives manually-input device information. In various alternative embodiments, a similar interface may provide a button to activate functionality to read some or all of the information to be input into the interface 1100 directly from the medicament device or packaging thereof. For example, such a button may engage a camera of the mobile device for the user to take a picture of a QR code or alphanumeric characters conveying the information. Then, through decoding (e.g., QR decoding or optical character recognition) the image data, the application may fill out some or all of the interface automatically. As another example, a button may engage nearby wireless communication (e.g., RFID, NFC, Bluetooth, Wifi, etc.) with a tag disposed on the medicament device or packaging thereof to extract digital information. The application may then autofill some or all of the fields on the interface 1100.

In various embodiments, such as those wherein the application will periodically communicate with the medicament device or packaging thereof, the device may register a unique or other id of the medicament device or packaging such that future communications may be correlated to the appropriate device. This identifier may be assigned to or read from the medicament device or packaging by the mobile device.

Figure 12:
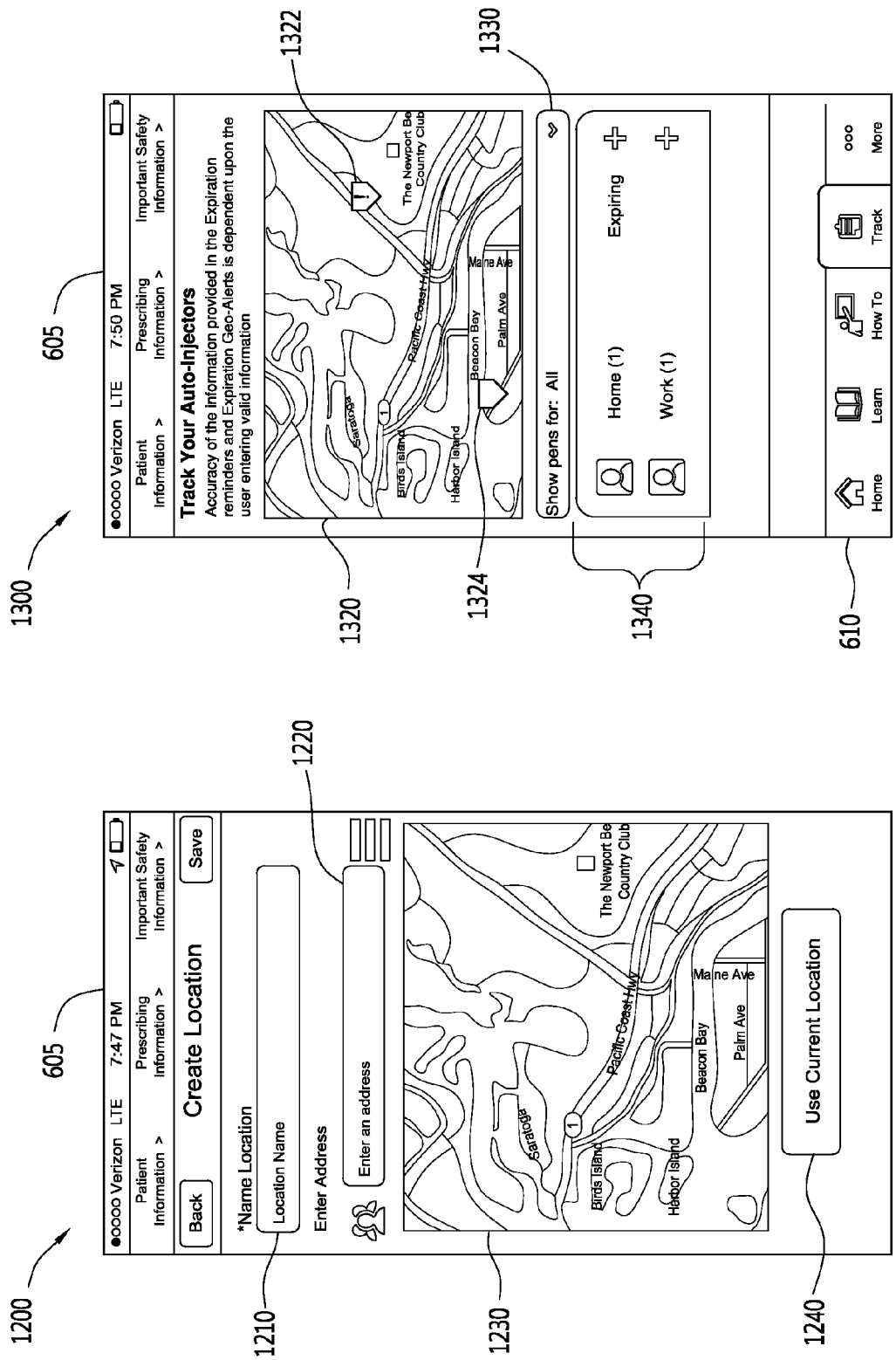
FIG. 12 illustrates a seventh exemplary user interface for a medicament device tracking application.

FIG. 12 illustrates a seventh exemplary user interface 1200 for a medicament device tracking application. The interface 1200 may be an interface for registering a new location, such as a location for a new medicament device registered via user interface 1100. As shown, the user interface 1200 includes a location name field 1210 for receiving a textual name or description of the location to be registered. The user interface 1200 may also include multiple functionalities for defining a location. As a first method, the user may present a street address in an address field 1220. The street address may be manually input or imported from a phone contact list or from another application. Upon entering an address, a map area 1230 may update to show a map of the area around the identified location.

As an alternative method, the user may select a location by tapping on the map. As yet another alternative, the user may press a "use current location" button to select a current location of the mobile device itself (e.g., as reported by a GPS function of the mobile device) as the location of the medicament device.

In various embodiments, the various profile, medicament device, and location information input into the application may also be downloaded into respective memory devices of one or more medicament devices. For example, the application may send appropriate name, allergen, and emergency contact information to each medicament device registered for that particular patient. Such communication may be, for example, performed wirelessly via NFC, RFID, Bluetooth, Wifi, or other communications protocols.

Figure 13:
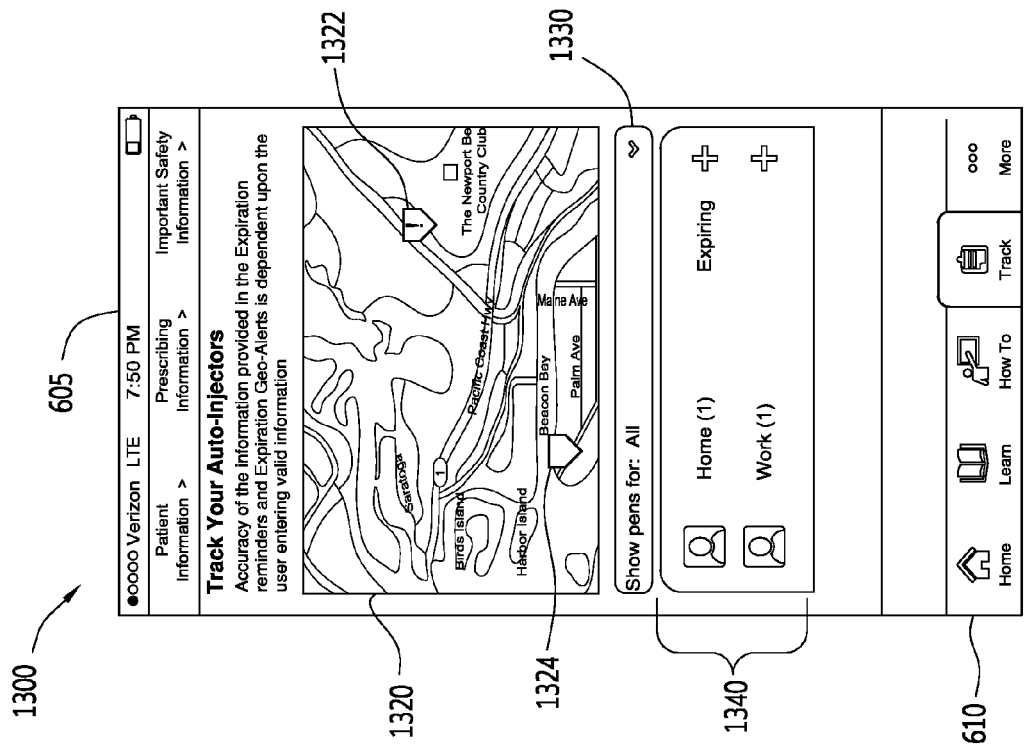
FIG. 13 illustrates a eighth exemplary user interface for a medicament device tracking application.

FIG. 13 illustrates an eighth exemplary user interface 1300 for a medicament device tracking application. The user interface 1300 may be an interface for tracking the location or other status of various registered medicament devices as may be accessed, for example, by selection of the "track your auto-injectors" button 935 of exemplary interface 900. The user interface 1300 includes a map 1320 for showing a nearby or otherwise relevant area. The map 1320 also includes one or more markers 1322, 1324 designating the location of the respective medicament devices. An alert icon 1322 communicates that some event, such as for example an expiration event (e.g., previous expiration or prospective expiration in the near future), is associated with the correlated medicament device.

A filter selector 1330 enables selection of one or more profiles or groups thereof. Upon selection of a profile or group of profiles, any indications 1322, 1324 not associated with the selected profiles will no longer be displayed on the map 1320. A medicament device list 1340 provides a summary of tracked medicament devices (along with associated location or any raised alarms) as filtered by the filter selector 1330. The medicament device list 1340 may further allow a user to select a medicament device to access a summary page specifically for that device or a medicament device edit page similar to, for example, user interface 1100.

The user interface 1300 may be additionally used to implement various features described above. For example, where the application receives periodic updates of the medicament device's location, the position of the indicators 1322, 1324 may be updated to correspond to the most recently-received location data for each respective medicament device. As another example, where the application receives indications of medicament usage from the medicament devices, the indicators 1322, 1324 may be updated to include an alert informing the user of medicament device usage. The alert may be placed on the map at the current location of the used medicament device, at a location where the medicament device was activated, at a location of another mobile phone or application associated with the medicament device (e.g., a child or spouse's mobile phone where the tracked medicament device has been prescribed to a child or spouse of the application user), or elsewhere as appropriate. Additionally or alternatively, the application may output an audio, visual, or tactile alert through an operating system element, such as the notifications bar 605. The user interface 1300 may also output information such as medicament temperature or color information.

As another example, selection of an expired or expiring medicament device via the map 1320 or device list 1340 may enable the user to order a replacement medicament device or schedule an appointment with an associated health service provider to receive an additional prescription. Alternatively, in some embodiments the application may perform these functions automatically upon identification of an expiration event. In some embodiments, the application may forward any indications of medicament device activation to emergency contacts assigned to the patient profile, either through standard channels such as telephone or email, or to a similar application executing on a mobile device of the emergency contact. Various additional application implementation details will be apparent in view of the foregoing functionalities.

Figure 14:
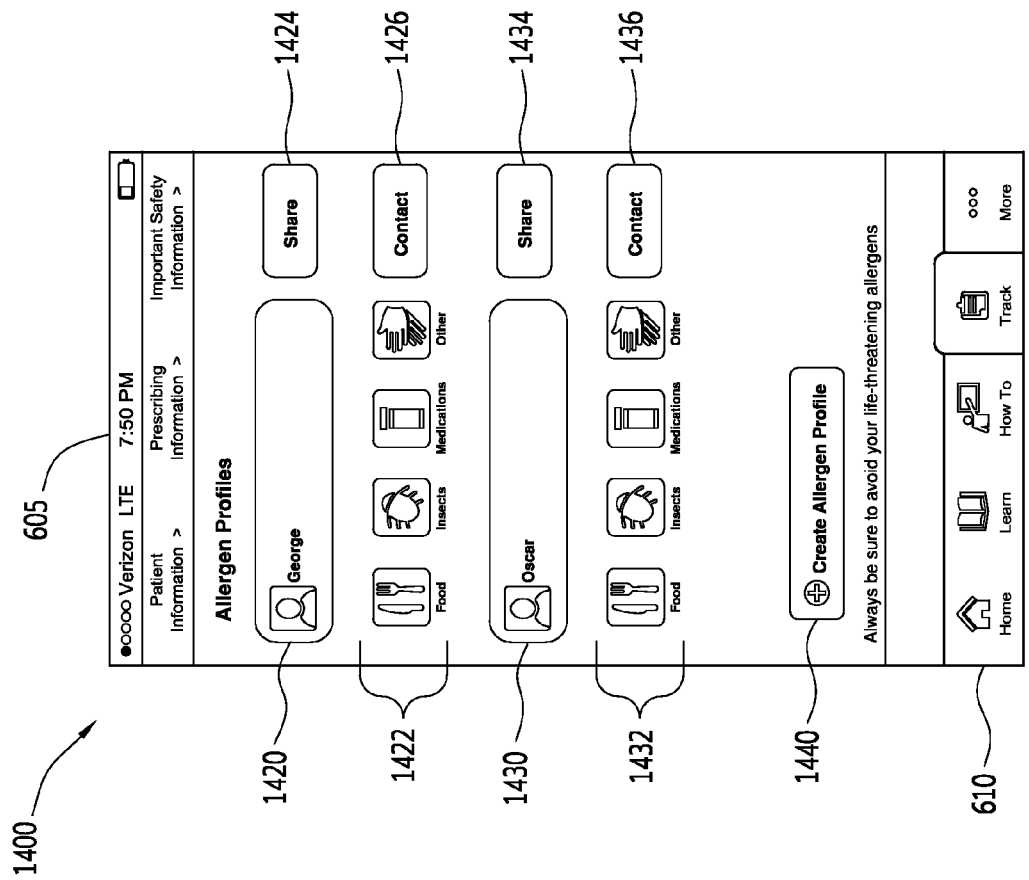
FIG. 14 illustrates a ninth exemplary user interface for a medicament device tracking application.

FIG. 14 illustrates a ninth exemplary user interface 1400 for a medicament device tracking application. The user interface 1400 may be an interface for reviewing, sharing, and editing allergen profiles accessed by, for example, by selection of the "allergen profiles" button 930 of exemplary interface 900. As shown, the user interface includes profile buttons 1420, 1430 associated with two different patient profiles. Selection of either button may take the user to a profile edit page such as, for example, an interface similar to user interface 1000. Below the respective profile buttons 1420, 1430, the user interface 1400 includes allergen summary icons 1422, 1432 indicating the allergies of the associated patient. Selection of the icons 1422, 1432 may direct the user to a more detailed listing of that patient's specific allergies as previously entered. A share button 1424, 1434 enables the user to share the associated patient profile with other devices such as, for example, through email, telephone, or directly to a similar application executing on a different device through, for example, NFC, RFID, Bluetooth, Wifi, etc. A contact button 1426, 1436 may enable the user to contact one or more emergency contacts registered for the patient via, for example, telephone, email, instant messaging, etc. Finally, a create allergen profile button 1440 enables to user to create additional patient profiles for subsequent display on the interface 1400.

According to the foregoing, various exemplary embodiments provide for systems and methods for distributing medicaments. In particular, by providing remote access to a medicament storage case, medicaments can be provided to patients in an emergency.

It should be apparent from the foregoing description that various exemplary embodiments of the invention may be implemented in hardware and/or firmware. Furthermore, various exemplary embodiments may be implemented as instructions stored on a machine-readable storage medium, which may be read and executed by at least one processor to perform the operations described in detail herein. A machine-readable storage medium may include any mechanism for storing information in a form readable by a machine, such as a personal or laptop computer, a server, or other computing device. Thus, a machine-readable storage medium may include read-only memory (ROM), random-access memory (RAM), magnetic disk storage media, optical storage media, flash-memory devices, and similar storage media.

It should be appreciated by those skilled in the art that any block diagrams herein represent conceptual views of illustrative circuitry embodying the principals of the invention. Similarly, it will be appreciated that any flow charts, flow diagrams, state transition diagrams, pseudo code, and the like represent various processes which may be substantially represented in machine readable media and so executed by a computer or processor, whether or not such computer or processor is explicitly shown.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

What is claimed is:

1. A method of tracking a status of a medicament device by a mobile device, the method comprising:
   receiving, by the mobile device, information regarding a medicament device, the information comprising location information and expiration information;
   determining a current location of the mobile device;
   determining, based on comparing the current location to the location information, that the medicament device is within a predetermined distance from the mobile device;
   determining, based on the received expiration information, that the medicament device is currently associated with an expiration event;
   outputting, to the user of the mobile device and via an operating system element of the mobile device configured to output notifications from multiple different applications, an expiration alarm indicating the expiration event in response to determining that the medicament device is within a predetermined distance from the mobile device and that the medicament device is currently associated with an expiration event;
receiving, from the user, a request to display a map of a geographic area;
displaying, by the mobile device and via a non-operating system application, the map of the geographic area; and
displaying an alert icon on the map, wherein the location of the icon on the map is based on the received location information.

2. The method of claim 1, wherein the mobile device receives the information regarding the medicament device by optically reading the information from at least one of the medicament device and a packaging of the medicament device.

3. The method of claim 1, wherein the mobile device receives the information regarding the medicament device by wirelessly communicating with at least one of the medicament device and a packaging of the medicament device.

4. The method of claim 1, wherein the expiration information is an expiration date and the expiration event comprises at least one of a past expiration of the medicament device and an expiration of the medicament device at a future date that is less than a predetermined amount of time from a current date.

5. The method of claim 1, wherein the mobile device receives the location information from the medicament device via a communications network, whereby the mobile device is capable of receiving the location information from the medicament device when the medicament device is at a location that is remote from the mobile device.

6. The method of claim 1, further comprising:
receiving, by the mobile device via a communications network, an activation indication that a second medicament device has been activated;
outputting an activation alert to the user based on the activation indication.

7. The method of claim 1, further comprising:
periodically polling a second medicament device using wireless communication to estimate a distance between the second medicament device and the mobile device;
determining, based on the estimated distance, that the second medicament device is farther away from the mobile device than a predetermined allowable distance; and
outputting a missing device alarm in response to determining that the second medicament device is farther away from then mobile device than the predetermined allowable distance.

8. A mobile device for tracking a status of a medicament device by a mobile device, the device comprising:
a communications interface;
a memory; and
a processor in communication with the communications interface and the memory, wherein the processor is configured to:
receive information regarding a medicament device, the information comprising location information and expiration information,
determine a current location of the mobile device,
determine, based on comparing the current location to the location information, that the medicament device is within a predetermined distance from the mobile device,
determine, based on the received expiration information, that the medicament device is currently associated with an expiration event,
output, to the user of the mobile device and via an operating system element configured to output notifications from multiple different applications, an expiration alarm indicating the expiration event in response to determining that the medicament device is within a predetermined distance from the mobile device and that the medicament device is currently associated with an expiration event,
receive, from the user, a request to display a map of a geographic area,
display, via a non-operating system application, the map of the geographic area, and
display an alert icon on the map, wherein the location of the icon on the map is based on the received location information.

9. The mobile device of claim 8, wherein, in receiving the information regarding the medicament device, the processor is configured to optically read the information from at least one of the medicament device and a packaging of the medicament device.

10. The mobile device of claim 8, wherein, in receiving the information regarding the medicament device, the processor is configured to wirelessly communicate with at least one of the medicament device and a packaging of the medicament device.

11. The mobile device of claim 8, wherein the expiration information is an expiration date and the expiration event comprises at least one of a past expiration of the medicament device and an expiration of the medicament device at a future date that is less than a predetermined amount of time from a current date.

12. The mobile device of claim 8, wherein, in receiving the location information, the processor is configured to receive the location information from the medicament device via a communications network, whereby the mobile device is capable of receiving the location information from the medicament device when the medicament device is at a location that is remote from the mobile device.

13. The mobile device of claim 8, wherein the processor is further configured to:
receive, by the mobile device via a communications network, an activation indication that a second medicament device has been activated;
output an activation alert to the user based on the activation indication.

14. A non-transitory machine-readable storage medium encoded with instructions for execution by a mobile device for tracking a status of a medicament device, the medium comprising:
instructions for receiving, by the mobile device, information regarding a medicament device, the information comprising location information and expiration information;
instructions for determining a current location of the mobile device;
instructions for determining, based on comparing the current location to the location information, that the medicament device is within a predetermined distance from the mobile device;
instructions for determining, based on the received expiration information, that the medicament device is currently associated with an expiration event;
instructions for outputting, to the user of the mobile device and via an operating system element of the mobile device configured to output notifications from multiple different applications, an expiration alarm indicating the expiration event in response to determining that the medicament device is within a predetermined distance from the mobile device and that the medicament device is currently associated with an expiration event;

instructions for receiving, from the user, a request to display a map of a geographic area;

instructions for displaying, by the mobile device and via a non-operating system application, the map of the geographic area; and instructions for displaying an alert icon on the map, wherein the location of the icon on the map is based on the received location information.

15. The non-transitory machine-readable storage medium of claim 14, wherein instructions for receiving the information regarding the medicament device comprise instructions for optically reading the information from at least one of the medicament device and a packaging of the medicament device.

16. The non-transitory machine-readable storage medium of claim 14, wherein the instructions for receiving the information regarding the medicament device comprise instructions for wirelessly communicating with at least one of the medicament device and a packaging of the medicament device.

17. The non-transitory machine-readable storage medium of claim 14, wherein the expiration information is an expiration date and the expiration event comprises at least one of a past expiration of the medicament device and an expiration of the medicament device at a future date that is less than a predetermined amount of time from a current date.

18. The non-transitory machine-readable storage medium of claim 14, wherein the instructions for receiving the location information comprise instructions for receiving location information from the medicament device via a communications network, whereby the mobile device is capable of receiving the location information from the medicament device when the medicament device is at a location that is remote from the mobile device.

19. The non-transitory machine-readable storage medium of claim 14, further comprising:

instructions for receiving, by the mobile device via a communications network, an activation indication that a second medicament device has been activated;

instructions for outputting an activation alert to the user based on the activation indication.

20. The non-transitory machine-readable storage medium of claim 14, further comprising:

instructions for periodically polling a second medicament device using wireless communication to estimate a distance between the second medicament device and the mobile device;

instructions for determining, based on the estimated distance, that the second medicament device is farther away from the mobile device than a predetermined allowable distance; and instructions for outputting a missing device alarm in response to determining that the second medicament device is farther away from then mobile device than the predetermined allowable distance.

* * * * *